United States Patent [19]

Lilga et al.

[11] Patent Number: 4,952,713

[45] Date of Patent: Aug. 28, 1990

[54] BRIDGED TRANSITION-METAL COMPLEXES AND USES THEREOF FOR HYDROGEN SEPARATION, STORAGE AND HYDROGENATION

[75] Inventors: Michael A. Lilga; Richard T. Hallen, both of Richland, Wash.

[73] Assignee: Battelle Memorial Institute, Richland, Wash.

[21] Appl. No.: 202,097

[22] Filed: Jun. 2, 1988

[51] Int. Cl.$^5$ .......................... C07F 7/02; C07F 11/00; C07F 15/02; C07F 15/06

[52] U.S. Cl. ........................................ 556/60; 556/11; 556/31; 556/32; 556/41; 556/47; 556/48; 556/58; 556/142; 556/144; 556/145

[58] Field of Search .................... 556/60, 142, 11, 47, 556/31, 32, 41, 48, 144, 145, 58

[56] References Cited

U.S. PATENT DOCUMENTS 3,064,024  11/1962  Wilkinson ............................. 556/60
3,326,948   6/1967  Cais et al. ............................. 556/60

OTHER PUBLICATIONS

Bitterwolf, Bis(cyclopentadienylthallium) Methane, etc., Journal of Organometallic Chemistry, 312 (1986), pp. 197–206.

Bryndza et al., Reaction of a Bridged Binuclear Dialkyl Cobalt Complex, etc., Journal of American Chemistry Soc., 101.16 (1979), pp. 4766–4768.

Collman et al., *Principles and Applications of Organotransition Metal Chemistry*, Mill Valley, CA; University Science Books, 1980.

Huheey, *Inorganic Chemistry*, New York; James E. Huheey, 1978.

*Primary Examiner*—Paul F. Shaver
*Attorney, Agent, or Firm*—Dellett, Smith-Hill and Bedell

[57] ABSTRACT

The present invention constitutes a class of organometallic complexes which reversibly react with hydrogen to form dihydrides and processes by which these compounds can be utilized. The class includes bimetallic complexes in which two cyclopentadienyl rings are bridged together and also separately $\pi$-bonded to two transition metal atoms. The transition metals are believed to bond with the hydrogen in forming the dihydride. Transition metals such as Fe, Mn or Co may be employed in the complexes although Cr constitutes the preferred metal. A multiple number of ancilliary ligands such as CO are bonded to the metal atoms in the complexes. Alkyl groups and the like may be substituted on the cyclopentadienyl rings. These organometallic compounds may be used in absorption/desorption systems and in facilitated transport membrane systems for storing and separating out $H_2$ from mixed gas streams such as the produce gas from coal gasification processes.

5 Claims, 1 Drawing Sheet

BRIDGED TRANSITION-METAL COMPLEXES AND USES THEREOF FOR HYDROGEN SEPARATION, STORAGE AND HYDROGENATION

This invention was made with government support under contract number DE-AC06-76RLO 1830, awarded by the U.S. Department of Energy. The government has certain rights in the invention.

BACKGROUND OF THE INVENTION

This invention relates to reversible hydrogenation reactions usable for $H_2$ separation or storage or in chemical synthesis, and particularly to a class of bridged bimetallic transition metal compounds that are useful as catalysts for such reactions.

The chemical reactions of molecular hydrogen have use in the hydrogenation of unsaturated hydrocarbons and similar compounds, and in processes for $H_2$ separation and storage. In particular, the selective separation or purification of $H_2$ from the product gas of coal gasification would be highly desirable. However, gas separation has in the past been a difficult and energy intensive process. The development of new and innovative techniques for selectively and efficiently separating specific gas components from mixed-gas streams would significantly reduce the cost and complexity of product gas production and processing. For example, efficient $H_2$ separation from synthesis gas could help to make coal an attractive future source of $H_2$ for use as a fuel or chemical feedstock. In addition, this technology could have a significant impact on processes not directly associated with coal gasification in which $H_2$ is lost in waste streams. These processes may include ammonia manufacture, reduction of metallic oxide ores, and the hydrogenation of fats and oils. Thus, wide-ranging applications exist for $H_2$ separation and recovery technologies However, the chemical reactions used either for separation or purification of $H_2$ must be highly reversible and selective in order to be commercially attractive. The reactions that are currently used for such purposes tend to be either inefficient or non-selective. For example, the recovery of $H_2$ from Pressure Swing Adsorption (PSA) is on the order of only 80%. Furthermore, PSA is ineffective with feeds containing less than 50% of $H_2$. Membrane separation systems are inherently energy efficient, but existing commercial systems such as PRISM cannot separate $H_2$ from streams containing gases such as $CO_2$.

A significant factor in determining the efficiency and yield of any process for storing or recovering hydrogen is the type of catalyst employed. For example, U.S. Pat. No. 4,695,446 issued Sept. 22, 1987 to Bogdanovic, describes a method of separating $H_2$ from a hydrogen-poor gas mixtures by contacting the mixture with a type of "active" magnesium which has been doped with a transition metal. The active magnesium reacts with hydrogen from the mixture to form magnesium hydride. Hydrogen may then be recovered by thermally dehydrogenating the magnesium hydride. However, it is preferred to use homogeneous catalytic processes in order to provide commercially acceptable rates of reaction.

The bulk of the research with respect to hydrogenation catalysts has related to chemical synthesis and especially the hydrogenation of unsaturated compounds. A number of such hydrogenation catalysts have included transition metal organometallic complexes.

For example, U.S. Pat. No. 4,645,849 issued Feb. 24, 1987 to Lewis describes a method for hydrogenating olefins and alkynes wherein the unsaturated hydrocarbon is reacted with $H_2$ in the presence of certain "cyclometallated" complexes in which a transition metal such as palladium, platinum, cobalt or the like forms a 4–6 membered ring system with a covalently bonded carbon in a hydrocarbon chain and a ligand atom such as phosphorous, nitrogen, arsenic, oxygen or sulfur. Additionally, U.S. Pat. No. 4,670,621 issued June 2, 1987 to Walker describes the use of certain cyclopentadienyl transition metal complexes of iridium and osmium as dehydrogenation catalysts in the conversion of paraffins to olefins having a corresponding carbon skeleton. Also, U.S. Pat. No. 4,360,475 issued Nov. 23, 1982 to Pruett, et al describes a class of bimetallic cluster compounds consisting of ruthenium carbide octahedra linked through a Group IIIA metal atom which may be used for converting synthesis gas to hydrocarbons and oxygenates.

Several organometallic catalysts which have been used for purposes other than hydrogenation (or dehydrogenation) have employed the cyclopentadienyl group as a ligand. For example, U.S. Pat. No. 4,423,276 issued Dec. 27, 1983 to Johnson describes a class of cyclopentadienyl tantalum compounds useful for olefin isomerization, i.e., the switching of an internal double bond to a terminal double bond. The process seems to be peculiar to the Ta atom. Similarly, U.S. Pat. No. 4,153,576 issued May 8, 1979 to Karol, et al relates to the preparation of cyclopentadienyl chromium alkyl/aryl oxides and siloxides, for use primarily as catalysts in the polymerization of ethylene but also for use in scavenging oxygen and volatile sulfur compounds from various liquid and gaseous streams. However, these compounds must be used on a silicon support and activated with a silane. U.S. Pat. No. 4,086,408 issued Apr. 25, 1978 to Karol, et al further describes the modification of bis-cyclopentadienyl chromium [II] compounds used as supported catalysts on an inorganic oxide. These complexes are modified by addition thereto of oxygen containing compounds such as ethers in order to improve the impact strength and toughness of ethylene polymers made therewith. Also, Japanese Pat. No. J6 0092-297-A describes a catalyst for the synthesis of pyridine derivatives from alkynes and nitriles which may be produced by the reaction of eta 5-substituted cyclopentadienyl cobalt monohalides with polyenes having 1–16 carbon atoms.

In reactions with molecular hydrogen, the use of bimetallic complexes as catalysts has sometimes been preferred. For example, U.S. Pat. No. 4,605,751 issued Aug. 12, 1986 to Curtis, et al describes a class of heterobimetallic cluster compositions usable for the selective hydrogenation of carbon monoxide. The complex includes sulfur directly bonded into the cluster, a metal from the group consisting of Cr, Co and W, another metal from the group Fe, Co and Ni and two or more cyclopentadienyl groups. The catalyst is supported on a refractory base such as alumina. Also, U.S. Pat. No. 4,656,299 issued Apr. 7, 1987 to Fujii, et al describes a class of substituted cyclopentadienyl cobalt complexes including certain bimetallics that are usable as catalysts in the preparation of pyridine homologues. The bimetallic form of this complex has two cobalt atoms bonded directly together and further connected through a metallocyclic ring.

U.S. Pat. No. 4,361,497 issued Nov. 30, 1982 to Boldt, et al represents one instance in which catalysts of the cyclopentadienyl metal carbonyl type have been used for hydrogenation. However, these have been polymeric catalysts in which the metal complex is bound to a polymer carrier, either directly through the cyclopentadiene group or indirectly through a methylene bridge, a phenyl group or the like in lieu of a phosphine type linkage. However, as noted earlier, the use of homogeneous catalysts is preferred.

Homogeneous hydrogenation catalysts based upon bimetallic complexes of rhodium or iridium in combination with methyl-substituted cyclopentadienyl groups are described in U.S. Pat. No. 3,849,459 issued Nov. 19, 1974 to Maitlis, et al. A catalytic hydride is postulated to have a hydrogen atom in an unusual bridging position between the two metal atoms with further bridging between the metals being provided by Cl atoms. The catalytic activity described in the patent is attributed to the bridged hydrogen.

Other classes of bimetallic compounds have been described for which no catalytic activity has been indicated. For example, U.S. Pat. No. 3,097,153 issued July 9, 1963 to Hubel, et al discloses a class of organometallic complexes which include metals of the VI, VII, or VIII subgroups of the periodic table, including Cr. This class may include bimetallic species associated with multiple carbonyl groups. The various complexes are used to produce hydrogenated linear and cyclic organic compounds that are free of carbon-to-metal bonds by reaction with hydrogenation agents such as $LiAlH_4$. Similarly, U.S. Pat. No. 3,326,948 issued June 20, 1967 to Cais, et al describes a variety of ferrocene-like organometallic compounds which include cyclopentadienyl groups that are $\pi$-bonded to transition metal carbonyl groups in which the metal may be Cr, Fe or Mn. The class also includes a number of bimetallic compounds. However, Cais et al require that olefinic chain components be connected to the cyclopentadienyl groups.

The art as referenced above thus does not provide any more efficient or rapid means of removing $H_2$ from mixed gas streams or for reversibly storing hydrogen. Furthermore, it would be useful to identify a class of compounds that would not only store hydrogen, but would also serve as hydrogenation catalysts through such a hydrogen-storing mechanism. The present invention provides such a class of compounds.

SUMMARY OF THE INVENTION

The present invention is directed to a novel class of organometallic complexes that are highly selective and reversible in forming hydrides with molecular hydrogen. The class of compounds useful in the present invention includes bimetallic complexes in which pairs of unsaturated rings such as cyclopentadienyl groups are bridged together and separately $\pi$-bonded to the metal atoms. These complexes are useful for gas purification and hydrogen storage purposes and may be useful as hydrogenation catalysts. More specifically, the invention exhibits a novel principle in the identification and development of compounds that will react very rapidly and reversibly with molecular hydrogen. This principle involves converting a slow and incomplete bimolecular reaction into a faster reaction which is unimolecular.

The question of whether such a bridged bimetallic complex might provide any advantage in seeking to carry out reactions involving hydrogen does not seem to have been previously investigated. It has been discovered that by bridging together of two unsaturated ring systems such as cyclopentadienyl groups and by forming bimetallic complexes therewith, compounds have been produced which have surprising selectivity, reactivity and reversibility when reacted with molecular hydrogen. It seems to be the case that the complex in question reacts in a rapid unimolecular rather than a bimolecular fashion.

The analogous bimolecular reaction from the prior art is that reported by Fischer, et al, *Inorg. Synth.* 7, 1963, pp. 136–9, which takes place between a dimeric metal complex such as $[CpCr(CO)_3]_2$ and $H_2$ to form a monomeric hydride of the form $CpCr(CO)_3H$, in which Cp represents the cyclopentadienyl group. With this dimeric complex, it has been reported that hydrogen uptake occurs at 70° C. and 150 atmospheres of $H_2$ and that the monomeric hydride complex slowly evolves $H_2$ when heated to 80° C., its melting point. Although these reactions may not be fully understood, it appears that the Cr—Cr bond in the above unbridged bimetallic complex is broken to form hydride bonds. Each hydride then becomes a separate molecule. Since molecular hydrogen is diatomic, the reverse of the foregoing reaction must be bimolecular. Two separate hydride molecules must come together to yield $H_2$. The reaction is therefore kinetically disfavored.

We conceived of the idea of creating a divalent catalyst which, when reacted with $H_2$, will remain as a single molecule. It was discovered that pairs of cyclopentadienyl chromium carbonyl groups can be linked or bridged together by a methylene group or the like to form a chelating ligand of the form required. Reaction with $H_2$ then produces a single dihydride molecule. The reaction is highly reversible and goes rapidly to completion. This useful result is believed to be the consequence of the structure of the compounds in maintaining the hydrided Cr atoms in close proximity so that reactions with molecular hydrogen are more favored. Whether or not such a theoretical interpretation may be correct, the present invention provides a class of compounds that are useful for storing hydrogen, separating hydrogen from gas streams, and as hydrogenation catalysts. The class comprises organometallic complexes formed using transition metals that are $\pi$-bonded to unsaturated rings, those rings in turn being bridged together to maintain the metals in proximity to one another.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DETAILED DESCRIPTION OF THE INVENTION

Transition Metal Complexes

Figure 1:
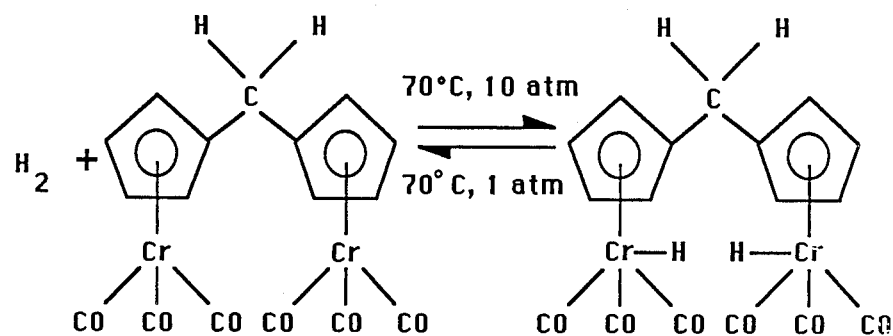
FIG. 1 illustrates the molecular structure of one example of the organometallic complex of the present invention and its hydride.

An example of one of the transition metal complexes of the present invention employs a methylene-bridged variant of the cyclopentadienylchromium tri-carbonyl dimer noted earlier as being reported by Fischer, et al. Synthesis of the unbridged compound has also been reported by King, et al, *Inorg. Synth.* 7, 1963, pp. 104–7.

In the synthesis of the bridged compound in accordance with the present invention, all reactions and manipulations are carried out in an inert atmosphere. In a typical preparation, 5 ml or 0.0608 moles of freshly cracked cyclopentadiene (CpH) is added to 1.4 grams of sodium sand in 100 ml of deoxygenated tetrahydrofuran (thf) and stirred until hydrogen evolution in accordance with Eq. (1) ceases:

$$2CpH + 2Na \rightarrow 2NaCp + H_2. \tag{1}$$

The resulting solution of sodium cyclopentadienide (NaCp) is removed from the excess Na, cooled to 0° C., and 2 ml or 0.028 moles of degassed $CH_2Br_2$ is added dropwise to bring about the reaction of Eq. (2):

$$2NaCp + Ch_2Br_2 \rightarrow CpCH_2Cp + 2NaBr. \tag{2}$$

The reaction vessel is then allowed to warm to room temperature, 1.4 grams of sodium sand is added, and the mixture is stirred overnight to allow the reaction of Eq. (3):

$$CpCH_2Cp + 2Na \rightarrow Na_2CpCH_2Cp + H_2. \tag{3}$$

The solution is then separated from the NaBr and excess sodium and transferred to a 500 ml flask containing 10 grams or 0.045 moles of $Cr(CO)_6$. To the mixture there is then added 100 ml of diglyme, and the thf is removed by vacuum. The diglyme solution is then heated in an oil bath to 160° C. for three hours until no more CO is evolved in accordance with Eq. (4):

$$Na_2CpCH_2Cp + 2Cr(CO)_6 \rightarrow Na_2(CpCH_2Cp)[Cr(CO)_3]_2 + 6CO. \tag{4}$$

The resulting solution is then cooled to room temperature and 150 ml or 0.042 moles of an aqueous solution of $Fe_2(SO_4)_3$ containing 9 ml of concentrated acetic acid is added to precipitate the crude product in accordance with Eq. (5):

$$Na_2(CpCH_2Cp)[Cr(CO)_3]_2 + 2Fe(III) \longrightarrow$$

$$(CpCH_2Cp)[Cr(CO)_3]_2 + 2Fe(II). \tag{5}$$

(I)

The precipitate I is filtered and washed with water, methanol and pentane. The green solid is dissolved in thf and passed through a column of neutral alumina. The purified product is obtained from the green eluate by solvent removal. Further purification may be achieved by recrystallization from thf/pentane. The infrared spectrum of the product in toluene shows bands at 2005, 1950 and 1927 cm$^{-1}$, and a UV/visible band at 450 nm.

The Cp groups in I are expected to be bonded at or near a tetrahedral angle from the methylene carbon. As will be further explained below, this angle is evidently adequate to hold the Cr atoms which are $\pi$-bonded to the Cp groups at positions which are sufficiently close to permit highly reversible hydride formation. Other chemical groups that are expected to act in the same fashion include $SiR_2$, —O—, —NR— (wherein R=Alkyl group) or —CO—. It may also be possible for the Cp rings in the complex to be bridged by an ethylene group or other (bridging) functionalities based on longer carbon chains. However, complexes bridged by ethylene or longer carbon chains may seek trans configurations in which the transition metal atoms are widely separated. The reversibility of hydride formation would be greatly decreased in complexes which prefer the trans configuration. Nonetheless, appropriate substitutions of bulky alkyl groups such as tertiary butyl or phenyl groups on the cyclopentadienyl rings or the bridging functionality might reverse this tendency, and allow longer bridging groups to be used.

It is believed transition metals other than Cr such as Fe, Mn or Co which are capable of $\pi$-bonding with Cp to form organometallic complexes and which have stable oxidation states at adjacent levels (separated by a single level) may also be used. The transition metals must have adjacent oxidation levels in order to allow the hydride formation reaction to take place.

Of course, the Cp group may be substituted thereon with any of a large number of alkyl groups or other groups which are non-reactive in the present context such as amine, ester or acyl groups. In particular, it may also be possible to substitute carboxylate groups on the Cp rings to enhance the solubility of the complex in aqueous solution.

It is also possible that the bridged complex may include ancillary two-electron ligands other than CO such as CNR.

The general formula for the compounds of the present invention may thus be given as $L_nMR_mCpXCpR'_{m'}M'L'_{n'}$ wherein:

Cp is the cyclopentadienyl ring;
$R_m$ and $R'_{m'}$ are alkyl groups or other non-reactive groups substituted for hydrogen on the Cp rings;
$L_n$ and $L'_{n'}$ are ancillary ligands taken from the group consisting of CO and CNR;
M and M' are transition metals taken from the group consisting of Cr, Fe, Mn and Co;
X is a bridging functionality taken from the group consisting of —$CH_2$—, $SiR_2$, —O—, —NR— (R=alkyl) and —CO—; and
n and n' represent integers from 1–6,
m and m' represent integers from 0–4.

Hydrogen Storage

Readily reversible $H_2$ binding is a requirement of any $H_2$ storage device. It is also necessary that $H_2$ be bound until release is desired. $H_2$ release can be affected by changes in temperature or partial pressure. The transition metal organometallic complex of the present invention can serve to take up $H_2$ under conditions of elevated temperature and pressure, store the $H_2$ at room temperature, and then release the $H_2$ when desired by again heating the hydrided complex to an elevated temperature under a relatively low partial pressure of hydrogen.

More specifically, compound I (of Eq. (5)) reacts reversibly with $H_2$ in accordance with Eq. (6):

$$(CpCH_2Cp)[Cr(CO)_3]_2 + H_2 \longrightarrow (CpCH_2Cp)[HCr(CO)_3]_2. \quad (6)$$

(II)

Compound II can be isolated by elution through neutral alumina and collection of the yellow eluate, for which the infrared spectrum in toluene shows bands at 2005 and 1925 $cm^{-1}$, and a UV/visible band at 345 nm.

The position of the equilibrium in Eq. (6) is both temperature and pressure dependent. In toluene solution, $H_2$ uptake does not occur at room temperature under 1 atm. of $H_2$, but does occur at 70° C. Uptake reaches 90% completion in about 3 hours at 70° C. and 7 atm.

Regeneration of hydrogen from the unbridged hydride can be achieved only to about 5%, by heating to 100° C. for two hours. $H_2$ is rapidly lost by photolysis, CO is also lost and an inactive complex is formed. On the other hand, regeneration of the bridged hydride and consequent recovery of the hydrogen, occurs much more rapidly and proceeds to 90% of its equilibrium concentration after 8 to 10 hours at 70° C. in a $H_2$ lean environment.

Hydrogen Separation

Systems for separating hydrogen from a gas stream which may take advantage of selective, reversible hydrogen binding by transition metal organometallic complexes include absorption/desorption systems and facilitated transport membrane systems.

Figure 2:
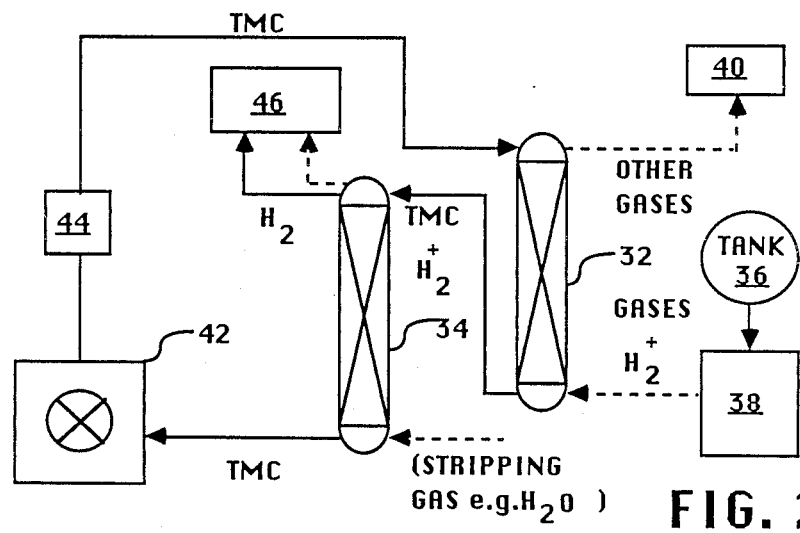
FIG. 2 is a block diagram of an absorber/stripper system which may be employed in practicing one embodiment of the present invention.

Referring now to FIG. 2, an absorption/desorption system 30 is shown including an absorber column 32 and a stripper column 34 both of which are adapted to provide counter-current flows of liquid and gas. A raw gas mixture containing hydrogen such as synthesis gas is supplied from a source such as the pressurized tanks 36 shown in FIG. 2 by way of the pressure and flow regulators 38 to the bottom of the absorber column 32. The gas proceeds vertically upward through the absorber column 32. At the same time a liquid solution containing one of the transition metal organometallic complexes of the present invention such as $(CpCH_2Cp)[Cr(CO)_3]_2$ which is dissolved in a high boiling aromatic solvent such as a xylene is pumped vertically downward through the absorber column 32. The absorber column 32 includes a packing material which helps to break up the gas mixture into a very large number of fine bubbles in order to maximize contact between the gas mixture and the liquid containing the organometallic complex. Operational conditions are controlled so that a temperature of about 70° C. and a partial pressure of $H_2$ in the range of 2–10 atmospheres (preferably 5–10 atm.) are maintained inside the absorber column 32.

The liquid solution takes up hydrogen from the stream of raw gas as the organometallic complex reacts to form its corresponding hydride, i.e., $(CpCH_2Cp)[CrH(CO)_3]_2$. The non-reactive gases from which the hydrogen has now been substantially removed are vented from the top of the column 32 to the outlet 40. The liquid solution now containing substantial amounts of the organometallic hydride is drawn off from the bottom of the column 32 and is directed into the top of the stripper column 34. This liquid solution flows vertically downward through the stripper column 34. However, operational conditions inside the stripper column 34 are controlled so that a temperature of about 70° C. is again maintained, but, at a reduced partial pressure of $H_2$ in the range of 0–1 atmosphere. At this lower pressure hydrogen gas is liberated from the liquid solution as the hydride of the organometallic complex reacts in a unimolecular fashion and produces hydrogen. The hydrogen gas flows vertically upwardly to where it can be removed from the top of the stripper column 34. Meanwhile the liquid solution which now contains the original (non-hydride) form of the organometallic complex is drawn off from the bottom of the stripper column 34 and supplied to the pump 42. The pump 42 drives the liquid solution back around to absorber column 32 through the pressure valve 44.

The hydrogen gas from the stripper column 34 should preferably be supplied to a condenser 46 which is operative for removing any solvent material which may be volatilized with the hydrogen gas. It should also be noted that a stripping gas such as water vapor (assuming the stripper column is operated at a somewhat higher temperature) may be employed to assist in removing the hydrogen from the liquid solution in the stripper column 34. The stripping gas would be directed vertically upward through the stripper column 34 and recovered in the condenser 46. For the efficient functioning of such a stripping gas the stripper column 34 should also contain a suitable packing material for breaking up the gas flow in the column.

Immobilized liquid membrane systems in which the organometallic complex of the present invention would act as a facilitated transport agent may offer the potential for high selectivity and increased flux. It does not appear that any commercially useful facilitated transport agents specific for $H_2$ have been previously identified. The present invention provides such an agent.

Figure 3:
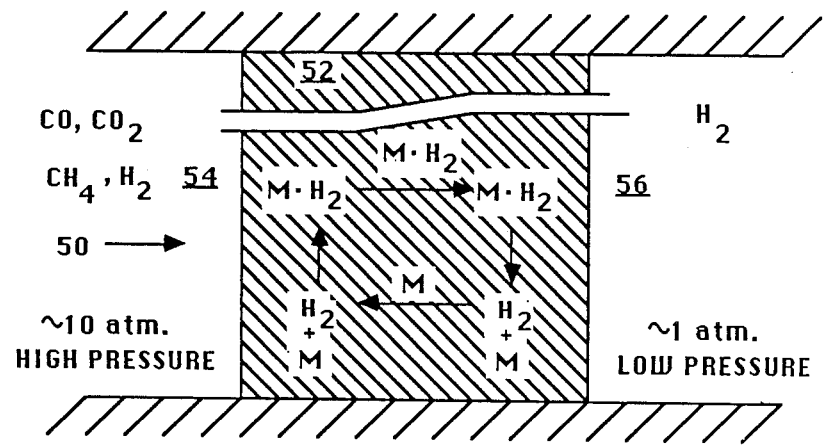
FIG. 3 is a graphic representation of a membrane system containing a dissolved metal complex in accor-

Referring now to FIG. 3, membrane system 50 for separating $H_2$ from a mixed gas stream includes a thin semi-permeable membrane 52 adapted for retaining a solution of the organometallic complex of the present invention within the membrane. The membrane 52 extends between a region having a high partial pressure of hydrogen such as 10 atm. on one side 54 and a region having a low partial pressure such as 1 atm. of hydrogen on its other side 56. Temperatures are maintained in the range of 70°–90° C. The driving force for separation is the pressure gradient across the membrane 52. On the high pressure side 54 of the membrane $H_2$ is removed from mixtures such as synthesis gas which may include other gases such as CO, $CO_2$, $CH_4$ and N. Hydrogen enters on the high pressure side 54 as indicated and then reacts with the transition metal organometallic complex (TMC) of the present invention in accordance with Eq. 7:

$$TMC + H_2 \rightarrow TMC - H_2. \quad (7)$$

(as also shown in Eq. 6)

The TMC-$H_2$ metal/hydrogen complex, or hydride, produces a concentration gradient under the influence of which it diffuses across the membrane 52 to the low pressure side 56. At the low pressure 56 side $H_2$ is released in an $H_2$-lean environment in accordance with Eq. 8:

$$TMC - H_2 \rightarrow TMC + H_2. \quad (8)$$

The $H_2$ is removed as it leaves the membrane 52. The concentration gradient of the organometallic complex is reinforced by the release of $H_2$, and drives the TMC un-hydrided metal complex back across the membrane 52 to the high pressure side 54. More $H_2$ is then taken up and bound thereto, thus causing the cycle to continue.

The function of the organometallic complex is to act as a specific carrier for $H_2$, and it therefore serves to increase the effective $H_2$ concentration in the membrane 52 relative to undesired gases. Selectivity for $H_2$ is particularly high when the organometallic complex of the present invention is used as described above which allows for thinner membranes to be employed and thus a greater flux.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. Bridged transition metal complex dihydride compounds of the general formula $$L_n MHCpR_m XCpR'_{m'} HM'L'_{n'},$$

wherein:
- $L_n$ and $L'_{n'}$ are ancillary ligands taken from the group consisting of CO and CNR,
- M and M' are transition metals taken from the group consisting of Cr, Fe, Mn and Co,
- Cp is the cyclopentadienyl group,
- R and R' are alkyl groups substituted for hydrogen on the Cp ring,
- m and m' represent integers from 0–4,
- n and n' represent integers from 1–6, and
- x is a bridging functionality taken from the group consisting of —$CH_2$—, $SiR_2$, —O—, —NR— (R=alkyl) and —CO—.

2. A compound as claimed in claim 1, wherein X is the methylene group.

3. A compound as claimed in claim 2, wherein M and M' are chromium.

4. A compound as claimed in claim 3, wherein $L_n$ and $L_{n'}$ are CO.

5. A compound as claimed in claim 4, wherein m and m'=0 and n and n'=3.

* * * * *

UNITED STATES PATENT AND TRADEMARK OFFICE
CERTIFICATE OF CORRECTION

PATENT NO. : 4,952,713
DATED : August 28, 1990
INVENTOR(S) : Michael A. Lilga and Richard T. Hallen It is certified that error appears in the above-identified patent and that said Letters Patent is hereby corrected as shown below:

Column 1, line 39, add a period (.) at the end of the paragraph.

Column 2, line 19, delete "carbide" and insert --carbido--.

Column 2, line 41, delete "bis-cyclopentadienyl" and insert --bis-cyclopentadienyl--.

Abstract, last line, delete "produce" and insert --product--.

Signed and Sealed this

Twenty-fifth Day of August, 1992

Attest:

DOUGLAS B. COMER

*Attesting Officer*    *Acting Commissioner of Patents and Trademarks*